(12) United States Patent
Chen et al.

(10) Patent No.: US 7,592,508 B1
(45) Date of Patent: Sep. 22, 2009

(54) **HIGH-EFFICIENCY *AGROBACTERIUM*-MEDIATED TRANSFORMATION OF COTTON USING PETIOLE EXPLANTS**

(75) Inventors: Zhi Xian Chen, Durham, NC (US); Lian Hui Zhang, Goldcoast Condominium (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 10/009,590

(22) PCT Filed: Jun. 11, 1999

(86) PCT No.: PCT/SG99/00058

§ 371 (c)(1),
(2), (4) Date: Apr. 3, 2002

(87) PCT Pub. No.: WO00/77230

PCT Pub. Date: Dec. 21, 2000

(51) Int. Cl.
*C12N 15/82* (2006.01)
(52) U.S. Cl. .................. 800/294; 435/469; 435/430
(58) Field of Classification Search .................. 800/294, 800/314; 435/431, 427
See application file for complete search history.

(56) References Cited

U.S. PATENT DOCUMENTS 5,846,797 A * 12/1998 Strickland .................. 800/294
2004/0087030 A1 * 5/2004 Armstrong et al. .......... 435/468

FOREIGN PATENT DOCUMENTS

| AU | 616444 | 11/1988 |
| JP | 01-160480 A | 6/1989 |
| WO | WO 97/12512 | 4/1997 |

OTHER PUBLICATIONS

Finer, 1988, Plant Cell Rep. 7:399-402.*
Price et al, 1979, Plant 145:305-307.*
Gawel, Nick J. et al., Somatic Embryo Genesis in Two *Gossypium hirsutum* Genotypes on Semi-Solid Versus Liquid Proliferation Media, Plant Cell Tissue and Organ Culture 23: 201-204, 1990.
Firoozabady, Ebrahim et al., "Transformation of Cotton (*Gossypium hirsutum* L.) by Agrobacterium Tumefaciens and Regeneration of Transgenic Plants," Plant Molecular Biology, 10:105-116 (1987), © Martinus Nijhoff Publishers, Dordrecht—Printed in the Netherlands.
Gawel, Nick et al., "Somatic Embryogenesis From Leaf and Petiole Callus Cultures of *Gossypium hirsutum* L.," Plant Cell Reports (1986), 5:457-459, © Springer-Verlag 1986.
English translation of Japanese Official Action dated Feb. 23, 2009, (2 pages).

* cited by examiner

*Primary Examiner*—Anne R Kubelik
(74) *Attorney, Agent, or Firm*—Rothwell, Figg, Ernst & Manbeck pc

(57) ABSTRACT

A method is disclosed for producing a transgenic cotton plant by *Agrobacterium*-mediated transformation of petiole tissue. The method comprises the steps of (a) obtaining cotton petiole explants, (b) exposing the petiole explants to a culture of *Agrobacterium tumefaciens* that harbors a vector comprising an exogenous gene and a selectable marker, the *Agrobacterium* being capable of effecting the stable transfer of the exogenous gene and selection agent resistance gene to the genome of the cells of the petiole explant, (c) culturing the petiole explants to induce callus formation, (d) selecting transformed callus that expresses the exogenous gene, (e) culturing the selected callus in suspension culture to induce formation of embryoids, (f) regenerating the embryoids into whole transgenic cotton plants.

17 Claims, 1 Drawing Sheet

HIGH-EFFICIENCY AGROBACTERIUM-MEDIATED TRANSFORMATION OF COTTON USING PETIOLE EXPLANTS

TECHNICAL FIELD

The present invention relates to the general field of genetic engineering of plants, in particular to the introduction of exogenous genetic material into cotton by *Agrobacterium* transformation of cotton petiole explants followed by somatic embryo regeneration.

BACKGROUND

Cotton is one of the most valuable and widely grown cash crops internationally. Its annual production worldwide is over 100 million bales valued at US$45 billion. Asia is the biggest cotton production area, with four out of five world top cotton producers located in this region. Cotton is not only the main supporter for the textile industry, but it also provides a huge and profitable market for manufacturers of chemicals for weed, disease and pest control. There are diverse opportunities for cotton molecular improvement, including improvement of yield and fiber quality and creation of new varieties that are resistant to herbicides, insects, nematodes and diseases (Steward, 1991).

Tissue Culture of Cotton: In 1935, Skovsted reported the first embryo culture of cotton. Beasley (1971) reported callus formation in cotton as an outgrowth from the micropylar end of fertilized ovules on Murashige & Skoog (MS) medium. Somatic embryogenesis was achieved from a suspension culture of *G. klotzschianum* (Price & Smith, 1979). In 1983, Davidonis & Hamilton first succeeded in efficient and repeatable regeneration of cotton (*G. hirsutum* L.) plants from callus after two-year cultivation. Cotton plants were since regenerated through somatic embryogenesis from different explants (Zhang & Feng, 1992; Zhang, 1994) including cotyledon (Davidonis et al., 1987; Davidonis & Hamilton, 1983; Finer, 1988; Firoozabady et al., 1987), hypocotyl (Cousins et al., 1991; Rangan & Zavala, 1984; Rangan & Rajasekaran, 1996; Trolinder & Goodin, 1988; Umbeck et al., 1987, 1989), stem (Altman et al., 1990; Bajaj et al., 1989; Chen, et al. 1987; Finer & Smith, 1984), shoot apex (Bajaj et al., 1985; Gould et al., 1991; Turaev & Shamina, 1986), immature embryo (Beasley, 1971; Stewart & Hsu, 1977, 1978), petiole (Finer & Smith, 1984; Gawel et al., 1986; Gawel & Robacker, 1990), leaf (Finer & Smith, 1984; Gawel & Robacker, 1986), root (Chen & Xia, 1991; Kuo et al., 1989), callus (Finer & McMullen, 1990; Trolinder et al., 1991) and protoplast (Chen et al., 1989).

Transformation of cotton: *Agrobacterium*-mediated cotton transformation was first reported a decade ago with hypocotyl and cotyledon as explants (Firoozabady et al., 1987; Umbeck et al., 1987). Several useful genes have been introduced into cotton via *Agrobacterium*-mediated transformation, including insect and herbicide resistance genes (Perlak et al., 1990; Trolinder et al., 1991; Chen et al., 1994). Explants (such as hypocotyl, cotyledon, callus generated from hypocotyl and cotyledon, as well as immature embryos) have been used for *Agrobacterium*-mediated transformation and particle bombardment (de Framond et al., 1983; Finer & McMullen, 1990; Firoozabady et al., 1987; Perlak et al., 1990; Rangan & Rajasekaran, 1996; Rajasekaran et al., 1996; Trolinder et al., 1991; Umbeck et al., 1987, 1989, 1992). In addition, meristematic tissue of excised embryonic axes has also been used for cotton transformation by particle bombardment (Chlan et al., 1995; John, 1996; John & Keller, 1996; McCabe & Martinell, 1993). Zhou et al. (1983) transformed cotton by injecting DNA into the axile placenta one day after self-pollination.

However, the transformation rates were generally low, ranging from 20 to 30% when hypocotyl were used as explant (Firoozabady et al., 1987; Cousins et al., 1991; Rajasekaran et al., 1996). A significantly higher transformation efficiency, up to 80%, was reported when cotyledon was used as explant and the ocs gene encoding octopine synthetase used as the reporter gene (Firoozabady et al., 1987). However, the validity of octopine as a marker for transformation is questionable because octopine has been found in several plant species certainly not transformed by infection with *A. tumefaciens* (Wendt-Gallitelli and Dobrigkeit, 1973). A more recent report indicated that the transformation efficiency of cotyledon was about 20 to 30% (Cousins et al., 1991). The transformation efficiency was even lower when particle bombardment method was used (Keller et al., 1997). A difference in the type of explants used for transformation could have a significant effect on the efficiency of transformation and regeneration. It has been reported, for example, that for reducing false positive transformants, cotyledon was a better explant than hypocotyledon (Firoozabady et al., 1987).

Cotton transformation also is highly dependent on genotype (Trolinder, 1985a, 1986; Trolinder & Goodin, 1987, 1988a, 1988b; Trolinder & Chen, 1989). Apart from a few cultivars which are regenerable and transformable, such as *Gossypium hirsutum* cv. Coker 312 and *G. hirsutum* Jin 7, most other important elite commercial cultivars, such as *G. hirsutum* cv. D&P 5415 and *G. hirsutum* cv. Zhongmian 12, are not regenerable and transformable by these methods. The absence of a high-efficiency plant regeneration method has been regarded as a major obstacle to the application of *Agrobacterium*-mediated transformation to cotton (Gawel et al., 1986; Firoozabady et al., 1987).

SUMMARY OF THE INVENTION

To overcome the problems associated with previously reported methods, an efficient transformation procedure using petiole as an explant has been developed, along with a set of correspondingly improved media. This method provides several advantages in comparison to the hypocotyl and cotyledon methods: (1) explants are easy to obtain; (2) transformation efficiency is higher; (3) *Agrobacterium* contamination is very rare; (4) efficiency in regeneration is higher; and (5) the time from transformation to regeneration of plantlets is reduced. Two cotton varieties, i.e. Coker 312 and Si-Mian 3, have been successfully transformed with this method, and more than 30 independent transgenic lines from Coker 312 showing strong activity of the marker transgene have been obtained. This method is applicable to other cotton varieties such as Jin 7 and Ji 713 from China, Siokra 1-3 from Australia, T25, Coker 201 and Coker 310 from the U.S.A.

DETAILED DESCRIPTION

Figure 1:
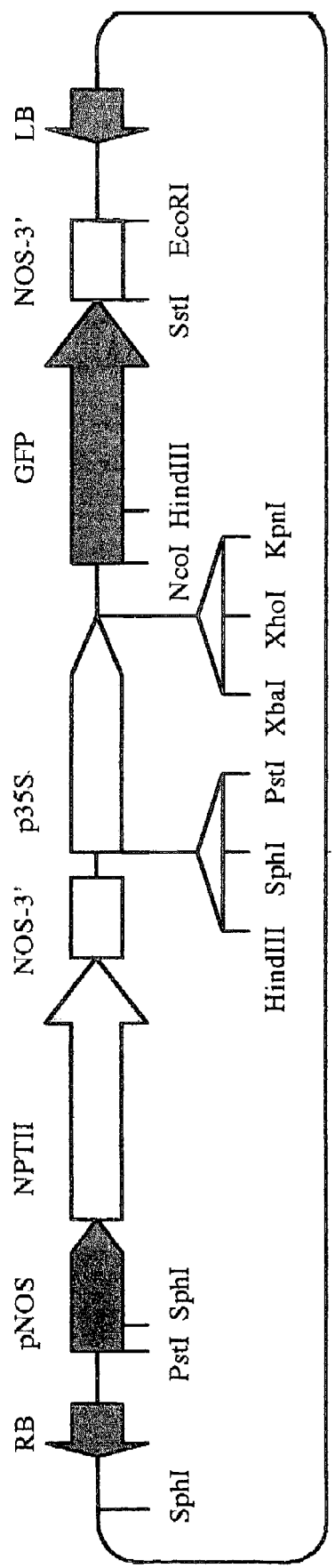
FIG. 1 shows the plasmid pBI121GFP, containing GFP as the reporter gene and the NPT II (neomycin phosphotransferase) gene as a selectable marker, used for *Agrobacterium*-mediated transformation of cotton petiole according to the methods of the present invention.

An efficient method is disclosed for genetic transformation of cotton plants, including elite lines, using cotton petiole as an explant. By using petiole explants, plus a set of improved media, transformation efficiency is significantly enhanced and the time required from transformation to regeneration is shortened in comparison to previously reported methods.

By using the methods of the present invention, the whole process from *Agrobacterium* transformation to the regeneration of transgenic plantlets can take about 6-7 months. The reported hypocotyl and cotyledon methods usually required 7-9 months or longer to complete the same process (Cousins et al., 1991; Chen et al., unreported observation). Another two months were required for growing the small plantlets to a suitable size for potting in soil.

Techniques for introducing exogenous genes into *Agrobacterium* such that they will be transferred stably to a plant or plant tissue exposed to the *Agrobacterium* are well-known in the art and do not form part of the present invention. It is advantageous to use a so-called "disarmed" strain of *Agrobacterium* or Ti plasmid, that is, a strain or plasmid wherein the genes responsible for the formation of the tumor characteristic of the crown gall disease caused by wild-type *Agrobacterium* are removed or deactivated. Numerous examples of disarmed *Agrobacterium* strains are found in the literature (e.g., pAL4404, pEHA101 and pEH 105 (Walkerpeach & Veltern, 1994)). It is further advantageous to use a so-called binary vector system, such as that described in Schilperoort et al., 1990, 1995. A binary vector system allows for manipulation in *E. coli* of the plasmid carrying the exogenous gene to be introduced into the plant, making the process of vector construction much easier to carry out.

Similarly, vector construction, including the construction of chimeric genes comprising the exogenous gene that one desires to introduce into the plant, can be carried out using techniques well-known in the art and does not form part of the present invention. Chimeric genes should comprise promoters that have activity in the host in which expression is desired. For example, it is advantageous to have a series of selectable markers for selection of transformed cells at various stages in the transformation process. A selectable marker (for example a gene conferring resistance to an antibiotic such as kanamycin, cefotaxime or streptomycin) linked to a promoter active in bacteria would permit selection of bacteria containing the marker (i.e., transformants). Another selectable marker linked to a plant-active promoter, such as the CaMV 35S promoter or a T-DNA promoter such as the NPT II NOS promoter, would allow selection of transformed plant cells. The exogenous gene that is desired to be introduced into the plant cell should comprise a plant-active promoter in functional relation to the coding sequence, so that the promoter drives expression of the gene in the transformed plant. Again, plant-active promoters, such as the CaMV 35S, the NPT II NOS promoter or any of a number of tissue-specific promoters, are well-known in the art and selection of an appropriate promoter is well within the ordinary skill in the art.

The present method can be used to produce transgenic plants expressing any number of exogenous genes, and is not limited by the choice of such a gene. The selection of the desired exogenous gene depends on the goal of the researcher, and numerous examples of desirable genes that could be used with the present invention are known in the art (e.g., the family of *Bacillus thuringiensis* toxin genes, herbicide resistance genes such as shikimate synthase genes that confer glyphosate resistance, U.S. Pat. No. 5,188,642, or a 2,4-D monooxygenase gene that confers resistance to 2,4-dichlorophenoxyacetic acid (2,4-D), Bayley et al., *Theoretical and Applied Genetics*, vol. 82, pp. 645-49, male sterility genes such as the antisense genes of U.S. Pat. No. 5,741,684 (Fabijanski, et al.), or even the elaborate crop protection systems described in U.S. Pat. No. 5,723,765 (Oliver et al.)).

Cotton regeneration is considered in the art to be heavily variety-dependant. The Coker series of cotton varieties have been shown to be relatively easy to transform. However, DP 5412, Zhongmain 12 and many other varieties still have difficulties associated with regeneration. The situation is the same for *G. barbadense* and other diploid species. While somatic embryogenesis and regeneration of whole plants is a highly genotype-dependent process in cotton, successful transformation and regeneration of two distinct cotton varieties, i.e. Coker 312 from U.S.A. and Si-Mian 3 from China, has been demonstrated using the methods of the present invention. It this therefor believed that the present invention has wide applicability to transformation of a variety of cotton lines.

Transgene integration in the genome of cotton produced by the methods of the present invention was confirmed using standard Southern hybridization techniques, as can identification of the copy number of the inserted transgene in each transgenic line (see Example 6, below). The F1 generation of transgenic cotton can be tested for the presence of the transgene, and inheritance pattern of the transgene in the F1 generation can be analyzed to confirm stability and inheritability.

As compared with other reported protocols, the cotton transformation system of the present invention has higher transformation efficiency and survival rate. This is attributable to several factors. In the present invention, petiole was used as an explant for transformation. Different types of cotton explants can have significant effects on the efficiencies of plant transformation and regeneration (Firoozabady et al., 1987). Induction of somatic embryogenesis from petiole was reported previously. But regeneration was either unsuccessful or very poor (Finer and Smith, 1984; Gawel et al., 1986). With the present invention, the efficiency of regeneration was significantly improved by using the improved media discussed below. In a preferred embodiment, calli of high quality were obtained when tender petioles rich in parenchyma cell in primary vascular bundle tissue were cultured in the MMSI medium (described below) with low concentrations of 2,4-D and Kinetin.

With the present invention, the time for embryo induction in suspension culture can be shortened to 10-14 days, from a previously reported 3 weeks (Cousins et al., 1991). It was found that a shortened period of suspension culture treatment is important for high frequency induction of embryogenesis. It is also important for reducing production of abnormal embryos, since a high percentage of vitreous embryos that are poor in regeneration are produced when cotton calli are maintained in suspension culture for too long (Chen et al, unpublished observation).

For maximum cell growth at different stages except at the young plant growing stage, glucose was used as the sole carbon source. The amount of glucose in the media can be from about 10 to about 50 g/l, preferably about 30 g/l. At the young plant growing stage, glucose and sucrose at about 10 g/l respectively as carbon sources are preferable for promotion of healthy plantlets growth.

For growth of callus, embryogenesis and callus proliferation, pH range can be from 5.8 to 7.5, preferably pH 6.2-7.0, most preferably at pH 6.5. A medium of pH 7.0 is preferable for healthy root growth of plantlets.

For effective callus initiation and induction of the potency of embryogenesis, low concentrations of 2,4-D and kinetin in the callus induction and selection medium is important. The amount of 2,4-D can be from 0 to about 0.5 mg/l, preferably about 0.05 mg/l. The amount of kinetin can be from 0.0 mg/l to about 1.0 mg/l, preferably about 0.1 mg/l. In the callus differentiation stage and embryoid germination stage, best result were obtained when no plant hormone was added to the media.

The amino acids asparagine and glutamine are better nitrogen sources than inorganic ammonia nitrogen for specifically supporting embryoids germination and root development. In the embryoid germination medium, the amount of asparagine can be about 200 to about 1000 mg/l, preferably about 500 mg/l. The amount of glutamine can be about 500 to about 2000 mg/l, preferably about 1000 mg/l. With these optimized nitrogen sources, the growth of non-embryogenic calli was inhibited while the germination, growth and root development of embryoids were preferentially promoted.

At different stages of cotton transformation except co-culture with *Agrobacterium*, plant tissue and callus are preferably maintained at 28° C. but can be varied from 25-35° C. For effective transformation, temperature in co-culture stage should not be higher than 28° C. A light condition of 16 hrs. light (60-90, $\mu Em^{-2}S^{-1}$) and 8 hrs. dark per day is preferable for all stages of cotton transformation and regeneration.

Unlike previously reported transformation and regeneration protocols (Umbeck et al., 1987; Firoozabady et al., 1987, Cousins et al.), the media used in the present invention are optimized in several respects: (a) glucose is used as a sole carbon source in all culture media except in the medium used to culture young plants previous to planting out in the greenhouse; (b) the media is adjusted to higher pH value (6.5-7.0); (c) lower concentration of 2,4-D (0.05 mg/l) and kinetin (0.1 mg/l) is used only at callus initiation stage, no hormone is used at other stages; (d) asparagine and glutamine are used to replace inorganic ammoniac nitrogen in the medium used for embryoid germination. These modifications are adapted for the physiological requirement of cotton embryoid development and plantlet growth. It has been found that healthy embryoid development and plantlet growth, especially root system development, are largely attributable to these optimized media. For example, it has been found that asparagine and glutamine were better nitrogen source than inorganic ammonia nitrogen for supporting embryoid germination and root development. In the preferred MMS3 medium (described below), which contains asparagine and glutamine as the nitrogen source, the growth of non-embryogenic calli was inhibited while the germination, growth and root development of embryoids were preferentially promoted. Because of the healthy root development, the survival rate of potted transgenic cotton plants obtained by the methods of the present invention is almost 100%. With the reported hypocotyl and cotyledon protocols (Umbeck et al., 1987; Firoozabady et al., 1987), poor root development has been regarded as the main reason accounting for poor survival rate of potted transgenic cotton plants.

The following are preferred plant tissue culture media used in the Examples:

(1) Seedling Growing Medium (Per Liter):
  ½ MS basal salt mixture (Sigma M5524)
  0.9 g $MgCl_2.6H_2O$
  2.0 g gellan gum (Phytagel™, Sigma)
  pH 7.0

(2) Petiole Pre-Culture Medium (Per Liter):
  MS basal salt mixture
  0.9 g $MgCl_2.6H_2O$
  2.0 g gellan gum (Phytagel™, Sigma)
  pH 7.0

(3) Co-Culture Medium (Per Liter):
  MS basal salt mixture
  10 mg Thiamine-HCl
  1 mg Pyridoxine-HCl
  1 mg Nicotinic acid
  100 mg Myo-inositol
  0.05 mg 2,4-dichlorophenoxyacetic acid (2,4-D)
  0.1 mg Kinetin
  30 g Glucose
  0.9 g $MgCl_2.6H_2O$
  2.0 g gellan gum (Phytagel™, Sigma)
  pH 6.5

(4) MMS1—Callus Induction and Selection Medium (Per Liter)
  Co-culture medium
  50 mg Kanamycin
  500 mg Cefotaxime (5) MMS2—Differentiation Medium (Per Liter):
  MS basal salt mixture
  10 mg Thiamine-HCl
  1 mg Pyridoxine-HCl
  1 mg Nicotinic acid
  100 mg Myo-inositol
  1.9 g $KNO_3$
  30 g Glucose
  0.9 g $MgCl_2.6H_2O$
  2.0 g gellan gum (Phytagel™, Sigma)
  pH 6.5

(5) MMS3—Embryoid Germination Medium (Per Liter):
  3.8 g $KNO_3$
  440 mg $CaCl_2.H_2O$
  375 mg $MgSO_4.7H_2O$
  170 mg $KH_2PO_4$
  1 g Glutamine
  500 mg Asparagine
  43 mg EDTA ferric-Na salt
  MS micronutrients (Murashige and Skoog, 1962)
  10 mg Thiamine-HCl
  1 mg Pyridoxine-HCl
  1 mg Nicotinic acid
  100 mg Myo-inositol
  30 g Glucose
  0.9 g $MgCl_2.6H_2O$
  2.0 g gellan gum (Phytagel™, Sigma)
  pH 6.5

(7) Young Plant Growing Medium
  S&H medium Macro and Micro elements (Stewart and Hsu, 1977)
  10 mg Thiamine-HCl
  1 mg Pyridoxine-HCl
  1 mg Nicotinic acid
  100 mg Myo-inositol
  10 g Glucose
  10 g Sucrose
  0.9 g $MgCl_2.6H_2O$
  2.0 g gellan gum (Phytagel™, Sigma)
  pH 7.0

The following Examples are intended to illustrate the present invention, and not in any way to limit its scope, which is solely defined by the claims.

EXAMPLE 1

Agrobacterium Strain and Plasmids

*A. tumefaciens* strain LBA 4404 (pBI121GFP) was used for transformation of cotton petiole and young stem. The physical map of pBI121GFP is shown in FIG. 1, which contains GFP as a reporter gene and NPTII gene (encoding neomycin phosphotransferase) as a selectable marker. The GFP and NPTII genes are under the control of CaMV $^{35}$S promoter and nos promoter respectively.

For construction of pBI121GFP, a 720 bp XbaI-SstI fragment of GFP gene from the pGFP2 plasmid (from Dr. N. H. Chua, Rockefeller University, New York) was cloned into the same sites in plasmid vector pBI121 (Clontech) to replace the GUS gene. The pBI121GFP plasmid was introduced into *A. tumefaciens* LBA 4404 by electroporation.

EXAMPLE 2

Plant Material

Upland cotton varieties Coker 312 from the U.S.A. and Si-Mian 3 from Shanxi Cotton Research Institute in China were used in the experiments.

Tender petioles were collected from plants 8-12 weeks old grown in a greenhouse with low light conditions. The petioles were surface-sterilized with 70% ethanol for a few seconds, followed by 20% bleach solution (Clorox Co. USA, 1% available chlorine) for 20 min. After rinsing five times in sterilized water, the petioles were pre-cultured in MS medium for 3 days.

EXAMPLE 3

Plant Transformation

A single colony of *A. tumefaciens* strain LBA 4404 (pBI121GFP) was inoculated in liquid LB medium with 50 mg/L Rifampicin, 50 mg/L kanamycin and 100 mg/L streptomycin. The bacteria was grown overnight at 28° C. in a shaker of 200 rpm. The bacterium cultures were diluted using liquid MS medium to OD600=0.3.

The petiole and young stem were cut into about 2 cm long segments. The segments were soaked in the diluted bacterium suspension for 5 min, then transferred onto plastic plates (100×25 mm) containing a filter paper soaked in 50 ml of co-culture medium. The plates were kept in an incubator of 24° C. under continuous light for 48 hrs. The co-cultured explants were transferred onto MMS1 medium and incubated at 28° C. with 16 hrs light (60-90, $\mu Em^{-2}s^{-1}$) and 8 hrs dark per day. After 2-4 weeks calli were initiated at the cut ends of petiole segments. After 4-6 weeks kanamycin resistant calli had appeared, and the number of calli were counted and the expression of GFP gene was examined.

Under the fluorescence microscope, the untransformed control callus appeared red in colour, while the transformed callus expressing GFP gene displayed distinct green fluorescence. A total of 113 putative transformed calli were examined for GFP activity, the transformation frequency of GFP gene was 39.8% (Table 1). When petioles from cotton variety Si-Mian 3 were used for transformation, 11 calli were found GFP positive from 26 calli tested, transformation efficiency was 42.3%.

TABLE 1

Transformation frequencies of petioles from cotton Coker 312 and Si-Main 3

| Varieties | Number of calli tested | Number of GFP positive calli | GFP gene transformation frequency (%) |
|---|---|---|---|
| Coker 312 | 113 | 45 | 39.8 |
| Si-Mian 3 | 26 | 11 | 42.3 |

EXAMPLE 4

Induction of Somatic Embryogenesis and Plant Regeneration

The calli with vigorous growth and strong expression of GFP were selected and transferred into liquid MMS2 medium for suspension culture for 2 weeks. Friable cream-colored granular calli were selected and transferred to semi-solid differential medium, MMS2. After about 2 months a large number of embryoids were produced. Cytoplasmic dense embryogenic structures were gradually developed and large embryos were produced on the medium within 1-2 month. A short time of suspension culture treatment was very important, not only for high frequencies of embryogenesis induction, but also for production of embryoids of good quality. Expression of GFP gene was checked again and all were GFP positive.

The embryoids and embryogenic calli with strong GFP activity were transferred onto the MMS3 medium. After 1-2 months the plantlets that were about 1-2 cm in height with 1-2 true leaves and good root development were transferred to the Young Plant Growing Medium for about one month. About one month later, young plants with 6-8 leaves and about 10-15 cm in height were potted in soil and move to the glasshouse. All 30 potted transgenic plants survived and were found expressing GFP protein. The total time required to obtain transgenic plantlets using was under 7 months, and plantlets were reading for potting out in the greenhouse in about 2 additional months (see Table 2).

TABLE 2

The time frame from transformation of petiole segments to plant regeneration (Coker 312)

| Transformation | Callus obtained | Embryos appeared | Regeneration | Plants planted to green house | Flowering |
|---|---|---|---|---|---|
| Apr. 10, 1998 | May 26, 1998 | Jul. 29, 1998 | Nov. 1, 1998 | Dec. 31, 1998 | Feb. 14, 1999 |

EXAMPLE 5

Detection of GFP Protein Activity

The expression of GFP protein activity was detected using a Leica MZ FLIII Fluorescence stereo microscope with a 480/40 nM excitation filter and a 510 ηM barrier filter.

Green fluorescence of GFP gene can be easily distinguished in the transformed callus, embryoids, and young plantlets, with the untransformed control appeared red in colour under the fluorescence Stereo microscope. The exceptions were the untransformed roots, which appeared dim green under the fluorescence microscope, probably due to some chromophorous chemicals accumulated in roots. But the roots with GFP activity could still be identified because the green fluorescence produced by GFP protein was brighter and appeared more uniform. Under the blue light produced by the fluorescence stereo microscope, red fluorescence is clearly visible in untransformed green plant tissues that are enriched with chlorophyll such as leaf and stem. In GFP-positive green plant tissues, yellow fluorescence also was detected because of the overlapping of red and green fluorescence. However, the expression of GFP gene in petal and anther was poorer in comparison to that in other parts of plant.

EXAMPLE 6

Analysis of Transgenic Plants

Genomic DNA from putatively transformed lines and non-transformed control plants was purified according to Paterson et al. (1993). After digestion with EcoRI, which cuts in-between left border of T-DNA and Nos-3' terminator of the chimerical GFP gene (FIG. 1), DNA was separated on a 0.8% TAE agarose gel and transferred to Hybond-N membrane according to manufacturer's instructions. DNA was fixed to the membrane by UV crossing linking before hybridizing to the DIG labeled coding region of the GFP gene. Hybridized probe was detected with anti-DIG-AP conjugate according to manufacturer's instructions (BOEHRINGER MANNHEIM).

The genomic DNA samples from 11 randomly selected transgenic lines and 1 untransformed control plant were analyzed Southern hybridization, using the coding region of GFP gene as the hybridization probe. The data indicate that 7 out of 11 lines have a single copy, 3 lines have 2 copies, and 1 line has 6 copies of T-DNA insertion. The high percentage of transgenic lines with a single copy of T-DNA insertion suggests that this transformation protocol has less risk of gene silencing and undesirable insertion mutants.

REFERENCES CITED

Altman, D. W. et al. 1990. Economic Botany 40, 106.

Bajaj, Y. P. S. 1985. Theor. Appl. Genet. 70, 363.

Beasley, C. A. 1971. In vitro culture of fertilized cotton ovules. Biosci. 21, 906-7.

Chen Z. X., Liewellyn D. J., Fan Y. L., Li S. J., Guo S. D., Jiao G. L., and Zhao J. X. 1994. 2,4-D Resistant Transgenic Cotton Plants Produced by *Agrobacterium*-mediated gene Transfer. Scientia Agriculture Sinica 27(2): 3 1-37.

Chen, Z. X., Li, S. J., Yue, J. X., Jiao, G. L. and Liu S. X. 1989. Plantlet regeneration from protoplasts isolated from an embryogenic suspension culture of cotton (*Gossypium hirsutum* L.). Acta Botanica Sinica 31, 966-9.

Chen, Z. X., Trolinder, N. L. et al., 1987. Some characteristics of somatic embryogenesis and plant regeneration in cotton cell suspension culture. Scientia Agriculture Sinica 20, 6-11.

Chlan, C. A., Lin, J., Cary, J. W. and Cleveland, T. E. 1995. A procedure for biolistic transformation and regeneration of transgenic cotton from meristematic tissue. Plant Mol. Biol. Rep. 13, 31-7.

Cousins Y. L., Lyon B. R., and Llewellyn D. J. 1991. Transformation of Australian cotton cultivar: prospects for cotton improvement through genetic engineering Aust. J. plant physiol., 18, 481-494.

Davidonis, G. H., and Hamilton, R. H. 1983. Plant regeneration from callus tissue of *Gossypium hirsutum* L. Plant Sci. Lett. 32, 89-93.

Davidonis, G. H., Mumma, R. O. and Hamilton, R. H. 1987. Controlled regeneration of cotton plants from tissue culture. U.S. Pat. No. 4,672,035.

de Framond et al. 1983. Mini-Ti: a new vector strategy for plant genetic engineering. Bio/technology 1, 262-9.

Finer, J. J. and McMullen, M. D. 1990. Transformation of cotton (*Gossypium hirsutum* L.) via particle bombardment. Plant Cell Reports 8, 586-9.

Finer, J. J., and Smith R. H. 1984. Initiation of callus and somatic embryos from explants of mature cotton (*Gossypium klotzschianum* Anderss). Plant Cell Reports 3, 41-43.

Finer, J., 1988. Plant regeneration from somatic embryogenic suspension cultures of cotton (*Gossypium hirsutum* L.). Plant Cell Rep. 7, 399-402.

Firoozabady E., DeBoer D. L., Merlo D. J., Halls E. J., Anderson L. N., Raska K. A., Murray E. E. 1987. Transformation of cotton, *Gossypium hirsutum* L. by *Agrobacterium tumefaciens* and regeneration of transgenic plants. Plant Molecular Biology 10, 105 1 16.

Gawel N. J., Rao A. P., and Robacker C. 1986. Somatic embryogenesis from leaf and petiole callus cultures of *Gossypium hirsutum* L. Plant Cell Reports 5, 457-459.

Gawel, N. J. and Robacker, C. 1990. Genetic control of somatic embryogenesis in cotton petiole callus cultures. Euphytica 49, 249-53.

Gould, J., Banister, S., Hasegawa, O., Fahima, M. and Smith, R. H. 1991. Regeneration of *Gossypium hirsutum* and *G. barbadense* from shoot apex tissues for transformation. Plant Cell Reports 10, 12-6.

Hoekema et al. 1983. A binary plant vector strategy based on separation of Vir- and T-Region of the *Agrobacterium tumefaciens* Ti-plasmid. Nature 303, 179-80.

John, M. E. 1996. Structural characterization of genes corresponding to cotton fiber mRNA, E6: reduced E6 protein in transgenic plants by antisense gene. Plant Mol. Biol. 30, 297-306.

John, M. E. and Keller, G. 1996. Metabolic pathway engineering in cotton: Biosynthesis of polyhydroxybutyrate in fiber cells. Proc. Natl. Acad. Sci. USA 93, 12768-73.

Keller G., Spatola L., McCabe D., Martinell B., Swain W. X. and John M. E. 1997. Transgenic cotton resistant to herbicide bialaphos. Transgenic Research 6, 385-392.

Kuo, C. C. et al., 1989. Proc. Beltwide Cotton Prod. Res. Confs, 638.

McCabe, D. E. and Martinell, B. J. 1993. Transformation of elite cotton cultivars via particle bombardment of meristems. Bio/technol. 11, 596-8.

Murashige T., and Skoog F. 1962. A revised medium for rapid growth and bioassays with tobacco tissue culture. Physiol. Plant 15, 473-493.

Paterson, A. H., Brubaker, C. L., and Wendel J. F., 1993. A rapid method for extraction of cotton (*Gossypium* spp.) Genomic DNA suitable for RFLP or PCR analysis. Plant Mol. Biol. Rptr. 11, 122-127.

Perlak F. J., Deaton R. W., Armstrong T. A., Fuchs R. L., Sims S. R., Greenplate J. T., and Fischhoff D. A. 1990. Insect resistant cotton plants. Bio/Technology 8, 939-943.

Price, H. J. and Smith, R. H. 1979. Somatic embryogenesis in suspension cultures of *Gossypium klotzschianum* Anderss. Planta 145, 305-6.

Rangan, F. J. and Zavala, T. Ip. A. 1984. Somatic embryogenesis in tissue culture of *Gossypium hirsutum* L.). In Vitro 20, 256.

Rangan, R. and Rajasekaran, K. 1996. Regeneration of cotton plant in cell suspension culture. U.S. Pat. No. 5,583,036 (continued from U.S. Pat. Nos. 5,244,802, 1993 and 122, 200, 1987).

Rajasekaran K., Grula J. W., Hudspeth R. L., Pofelis S., Anderson D. M. 1996. Herbicide resistant Acala and Coker cotton transformed with the native gene encoding mutant forms of acetohydroxyacid synthase, Mol. Breeding, 2: 307-319.

Schilperoort, R. A., Hoekema, A., Hooykaas, P. J. J. 1990. Process for the incorporation of foreign DNA into the genome of dicotyledonous plants. U.S. Pat. No. 4,940,838.

Schilperoort, R. A., Hoekema, A., 1995. Process for the incorporation of foreign DNA into the genome of dicotyledonous plants. U.S. Pat. No. 5,464,763.

Steward J. McD. 1991. Biotechnology of Cotton: Achievements and Perspectives. CAB International.

Stewart J. McD., and Hsu C. L. 1977. In ovule embryo culture and seedling development of cotton (*Gossypium hirsutum* L.). Planta 137, 113-117.

Stewart, J. M. D. and Hsu, C. L. 1978. Hybridization of diploid and tetraploid cottons through in-ovulo embryo culture. J. Heredity 69, 404-8.

Trolinder, N. L. 1985a. Somatic embryogenesis and plant regeneration in cotton (*Gossypium hirsutum* L.). A Dissertation in Biology (December, 1985).

Trolinder, N. L., Chen, Z. X., 1989. Genotype specificity of the somatic embryogenesis response in cotton. Plant Cell Reports 8, 133-6.

Trolinder, N. L. and Goodin, J. E. 1987. Somatic embryogenesis and plant regeneration in cotton (*Gossypium hirsutum* L.). Plant Cell Reports 6, 231-4.

Trolinder, N. L. and Goodin, J. E. 1988a. Somatic embryogenesis and regeneration in cotton. I. Effects of source of explant and hormone regime. Plant Cell Tissue Organ Culture 12, 31-42.

Trolinder, N. L. and Goodin, J. E. 1988b. Somatic embryogenesis and regeneration in cotton. II. Requirements for embryo development and plant regeneration. Plant Cell Tissue Organ Culture 12, 43-53.

Trolinder N. L., Quisenberry J., Bayley C., Ray C., and Ow D. 1991. 2,4-D-resistant transgenic cotton. Proceedings, Beltwide Cotton Conferences. National Cotton Council, Memphis, Tenn., P840.

Turaev, A. M. and Shamina, Z. B. 1986. Soniet Plant Physiol. 33, 439.

Umbeck P. 1992. Genetic engineering of cotton plants and lines. U.S. Pat. No. 5,159,135.

Umbeck, P. F, Johnson, G., Barton, K. and Swain, W. 1987. Genetically transformed cotton (*Gossypium hirsutum* L.) plants. Bio/technol. 5, 263-6.

Umbeck P., Johnson P., Barton K., and Swain w. 1987. Genetically transformed cotton (*Gossypium hirsutum* L.) plants. Bio/Technology 5, 263-266.

Walkerpeach, C. R. and Veltern, J. 1994. *Agrobacterium*-mediated gene transfer to plant cells: cointegrate and binary vector systems. Plant Mol. Biol. Manual B1, 1-19.

Wendt-Gallitelli M. F., and Dobrigkeit I. 1973. Investigations implying the invalidity of octopine as a marker for transformation by *Agrobacterium tumefaciens*. Zeitschrift fur Naturforschung—Section C—Biosciences 28, 768-771.

Zhang, H.-B. 1994. The tissue culture of cotton (II). Plant Physiol. Commun. 30, 386-91.

Zhang, H.-B. and Feng, R. 1992. The tissue culture of cotton (I). Plant Physiol. Commun. 30, 386-91.

Zhou, G.-Y., Weng, J., Zeng, Y.-S., Huang, J.-G., Qian, S.-Y. and Liu, G.-L. 1983. Introduction of exogenous DNA into cotton embryos. Methods in Enzymology 101, 433-81.

We claim:

1. A method of producing a transgenic cotton plant comprising the steps of:
   (a) obtaining cotton petiole explants,
   (b) exposing the petiole explants to a culture of *Agrobacterium tumefaciens* that harbors a vector comprising an exogenous gene and a selectable marker gene in medium that does not contain plant hormones and contains glucose as the sole carbon source, the *Agrobacterium* being capable of effecting the stable transfer of the exogenous gene and selectable marker gene to the genome of the cells of the petiole explant,
   (c) culturing the petiole explants on a medium containing one or more plant hormones and contains glucose as the sole carbon source to induce callus formation, wherein the one or more plant hormones is 2,4-dichlorophenoxyacetic acid at a concentration up to about 0.5 mg/l and kinetin at a concentration up to about 1 mg/l and wherein the pH of the medium is from 6.5 to 7.0,
   (d) selecting a transformed callus that expresses the exogenous gene on a medium that does not contain plant hormones and contains glucose as the sole carbon source, wherein the pH of the medium is from 6.5 to 7.0,
   (e) culturing the selected callus in suspension culture in a medium that does not contain plant hormones and contains glucose as the sole carbon source for a duration of about 10 days to about 14 days to induce formation of embryogenic calli, wherein the pH of the medium is from 6.5 to 7.0,
   (f) culturing the embryogenic calli on a medium that does not contain plant hormones and contains glucose as the sole carbon source to induce formation of embryoids, wherein the pH of the medium is 6.5 to 7.0, and
   (g) germinating an embryoid on a medium that does not contain plant hormones, contains glucose as the sole carbon source and contains a source of nitrogen selected from the group consisting of asparagine at an amount of about 200 mg/l to about 1 g/l, glutamine at an amount of about 500 mg/l to about 2 g/l and both asparagine at an amount of about 200 mg/l to about 1 g/l and glutamine at an amount of about 500 mg/l to about 2 g/l to obtain a young transgenic cotton plant, wherein the aspargine, glutamine or asparagine and glutamine replaces ammonium nitrogen in the medium and wherein the pH of the medium is 6.5 to 7.0.

2. The method of claim 1, wherein the petiole explants are pre-cultured for a period of time prior to exposure to the culture of *Agrobacterium tumefaciens*.

3. The method of claim 1, wherein the glucose is at a concentration of about 10 g/l to about 50 g/l.

4. The method of claim 3, wherein the glucose is at a concentration of about 30 g/l.

5. The method of claim 1, wherein the medium in step (g) further contains KNO$_3$ as a further source of nitrogen at a concentration of about 3.8 g/l.

6. The method of claim 5, wherein the source of nitrogen in the medium in step (g) is at a concentration of about 700 mg/l to about 5 g/l.

7. The method of claim 1, wherein the source of nitrogen in the medium in step (g) is both asparagine and glutamine, and the asparagine is at a concentration of about 200 mg/l to about 1 g/l and the glutamine is at a concentration of about 500 mg/l to about 2 g/l.

8. The method of claim 7, wherein the asparagine is at a concentration of about 500 mg/l and the glutamine is at a concentration of about 1 g/l.

9. The method of claim 1, wherein the suspension culture of step (e) has a duration of about 14 days.

10. The method of claim 1, wherein the 2,4-dichlorophenoxyacetic acid is at a concentration of about 0.05 mg/l and the kinetin is at a concentration of about 0.1 mg/l.

11. The method of claim 1 which further comprises:
   (h) growing the young transgenic cotton plant on a medium that does not contain plant hormones and contains glucose and sucrose as the carbon source to produce a transgenic cotton plant capable of growth in soil.

12. The method of claim 11, wherein the medium in step (h) contains about 10 g/l of each of the glucose and the sucrose.

13. A method of producing a transgenic cotton plant comprising the steps of:
   (a) obtaining tender petiole explants from cotton plants,
   (b) exposing the petiole explants to a culture of *Agrobacterium tumefaciens* that harbors a vector comprising an exogenous gene and a selectable marker gene in a medium that does not contain plant hormones and contains glucose as the sole carbon source, the *Agrobacterium* being capable of effecting the stable transfer of the exogenous gene and selectable marker gene to the genome of the cells of the petiole explant,
   (c) culturing the petiole explants to induce callus formation on medium containing about 0.05 mg/l 2,4-dichlorophenoxyacetic acid and about 0.1 mg/l kinetin and glucose as the sole carbon source, wherein the pH of the medium is from 6.5 to 7.0,
   (d) selecting a transformed callus that expresses the exogenous gene on medium that does not contain plant hormones and contains glucose as the sole carbon source, wherein the pH of the medium is from 6.5 to 7.0,
   (e) culturing the selected callus in suspension culture in medium that does not contain plant hormones and contains glucose as the sole carbon source for a duration of about 10 days to about 14 days to induce formation of embryogenic calli, wherein the pH of the medium is from 6.5 to 7.0,
   (f) culturing the embryogenic calli on medium that does not contain plant hormones and contains glucose as the sole carbon source to induce formation of embryoids, wherein the pH of the medium is 6.5 to 7.0, and
   (g) germinating an embryoid on medium that does not contain plant hormones, contains glucose as the sole carbon source, contains KNO$_3$ at a concentration of 3.8 g/l and contains a further source of nitrogen selected from the group consisting of asparagine at an amount of about 200 mg/l to about 1 g/l, glutamine at an amount of about 500 mg/l to about 2 g/l and both asparagine at an amount of about 200 mg/l to about 1 g/l and glutamine at an amount of about 500 mg/l to about 2 g/l to obtain a young transgenic cotton plant, wherein the asparagine, glutamine or asparagine and glutamine replaces ammonium nitrogen in the medium and wherein the pH of the medium is 6.5 to 7.0.

14. The method of claim 13 which further comprises:
   (h) growing the young transgenic cotton plant on a medium that does not contain plant hormones and contains glucose and sucrose as the carbon source to produce a transgenic cotton plant capable of growth in soil.

15. The method of claim 14, wherein the medium in step (h) contains about 10 g/l of each of the glucose and the sucrose.

16. The method of claim 14, wherein the asparagine in the medium in step (g) is at a concentration of about 500 mg/l and the glutamine in the medium in step (g) is at a concentration of about 1 g/l.

17. The method of claim 13, wherein the suspension culture of step (e) has a duration of about 14 days.

* * * * *